(12) United States Patent
Xu et al.

(10) Patent No.: US 12,016,590 B2
(45) Date of Patent: Jun. 25, 2024

(54) FLEXIBLE PUNCTURE NEEDLE DEVICE

(71) Applicant: BEIJING SURGERII ROBOTICS COMPANY LIMITED, Beijing (CN)

(72) Inventors: Kai Xu, Beijing (CN); Yuyang Chen, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 515 days.

(21) Appl. No.: 17/292,563

(22) PCT Filed: Dec. 27, 2019

(86) PCT No.: PCT/CN2019/129327
§ 371 (c)(1),
(2) Date: May 10, 2021

(87) PCT Pub. No.: WO2020/135758
PCT Pub. Date: Jul. 2, 2020

(65) Prior Publication Data
US 2022/0000518 A1 Jan. 6, 2022

(30) Foreign Application Priority Data

Dec. 28, 2018 (CN) .......................... 201811619620.8

(51) Int. Cl.
*A61B 17/34* (2006.01)
(52) U.S. Cl.
CPC .. *A61B 17/3421* (2013.01); *A61B 2017/3454* (2013.01); *A61B 2017/348* (2013.01)
(58) Field of Classification Search
CPC ........ A61B 17/3421; A61B 2017/3454; A61B 2017/348; A61B 17/3478;
(Continued)

(56) References Cited

U.S. PATENT DOCUMENTS 6,059,739 A * 5/2000 Baumann .......... A61M 25/0136
604/95.01
2006/0064101 A1* 3/2006 Arramon .......... A61B 17/32002
606/82
(Continued)

FOREIGN PATENT DOCUMENTS

CN 101506538 A 8/2009
CN 101632572 A 1/2010
(Continued)

*Primary Examiner* — Richard G Louis
(74) *Attorney, Agent, or Firm* — SZDC Law PC (57) ABSTRACT

A flexible puncture needle device includes a puncture needle (10). The puncture needle (10) includes an outer tube (11) and a central tube (13). The outer tube (11) includes a puncture needle head (111) and a plurality of segments (112). The puncture needle head (111) includes a needle tip at front end and a pair of notches (1122) or a pair of protrusions (1121) at rear end, and a pair of protrusions (1121) and a pair of notches (1122) are formed at two ends of the segment (112), respectively. A pair of protrusions (1121) or a pair of notches (1122) at an end of the segment (112) are engaged with a pair of notches (1122) or a pair of protrusions (1121) at rear end of the puncture needle head (111) to form a needle head joint. Two adjacent segments (112) are engaged via the notches (1122) and the protrusions (1121) to form a joint, and the needle head joint and a plurality of joints are sequentially engaged with each other from head to tail to form an outer tube (11) with the puncture needle head (111) at tip end and a tube body capable of axially bending. Central tube (13) is inserted into the outer tube (11) from another end of the outer tube (11) away from the puncture needle head (111) to form a central tube vacant portion (114) and central tube insertion portion (115) of the outer tube (11). The central tube vacant portion (114) is capable of bending, and during the forward or backward movement of the central tube (13) in the outer tube (11)

(Continued)

along an axis of the outer tube (11). A bendable angle of the central tube vacant portion (114) changes as a length of the central tube vacant portion (114) changes.

16 Claims, 5 Drawing Sheets (58) Field of Classification Search
CPC .... A61B 2017/003; A61B 2017/00314; A61B 17/3401; A61B 17/3403; A61B 17/3417
See application file for complete search history.

(56) References Cited

U.S. PATENT DOCUMENTS

| | | |
|---|---|---|
| 2009/0281498 A1 | 11/2009 | Acosta et al. |
| 2010/0056862 A1 | 3/2010 | Bakos |
| 2010/0094269 A1 | 4/2010 | Pellegrino et al. |
| 2012/0265210 A1 | 10/2012 | Grinberg et al. |
| 2012/0279325 A1 | 11/2012 | Baena et al. |
| 2016/0022313 A1* | 1/2016 | Yoshida ............. A61B 17/3478 606/185 |
| 2016/0361088 A1 | 12/2016 | Maguire et al. |
| 2018/0242958 A1 | 8/2018 | Dayton et al. |

FOREIGN PATENT DOCUMENTS

| | | |
|---|---|---|
| CN | 103402576 A | 11/2013 |
| CN | 104394785 A | 3/2015 |
| CN | 104602615 A | 5/2015 |
| CN | 204600593 U | 9/2015 |
| CN | 105120932 A | 12/2015 |
| CN | 106175850 A | 12/2016 |
| CN | 109498126 A | 3/2019 |
| WO | 2018160401 A1 | 9/2018 |

* cited by examiner

FLEXIBLE PUNCTURE NEEDLE DEVICE

The present invention is the U.S. National Phase of International Application No. PCT/CN2019/129327, filed on Dec. 27, 2019, which claims priority to Chinese patent application No. 201811619620.8, filed on Dec. 28, 2018, entitled "Flexible Puncture Needle Device," which is incorporated herein by reference for all purposes as if fully set forth herein.

TECHNICAL FIELD

The disclosure relates to the technical field of medical instruments, in particular to a flexible puncture needle device.

BACKGROUND

Puncture needle is an instrument used for percutaneous puncture intervention operations. Compared with other operation methods, puncture operation can directly reach operation site so as to avoid exposing internal tissues and organs. Puncture operation is simple and convenient to operate, and is a minimally invasive diagnosis and treatment method.

A common puncture needle in the market, such as Seldinger needle, Chiba needle, etc., are elongated rigid structures. During the actual puncture process, because obstacles such as some important organs or tissues of a human body cannot be flexibly bypassed, the puncture process is difficult to accurately control. Moreover, the puncture needle may be deformed and deviate from a target. It is difficult to accurately position the puncture target. Auxiliary positioning needs to be performed through other medical imaging technologies.

SUMMARY

An objective of the present disclosure is to provide a flexible puncture needle device to solve the problems of bypassing obstacles and accurate positioning during puncture process.

The present disclosure provides a flexible puncture needle device comprising a puncture needle. The puncture needle comprises an outer tube and a central tube. The outer tube comprises a puncture needle head and a plurality of segments. The puncture needle head includes a needle tip at front end and a pair of notches or a pair of protrusions at rear end, and a pair of protrusions and a pair of notches are formed at two ends of the segment, respectively. A pair of protrusions or a pair of notches at an end of the segment are engaged with a pair of notches or a pair of protrusions at rear end of the puncture needle head to form a needle head joint. Two adjacent segments are engaged via the notches and the protrusions to form a joint, and the needle head joint and a plurality of joints are sequentially engaged with each other from head to tail to form an outer tube with the puncture needle head at tip end and a tube body capable of axially bending. Central tube is inserted into the outer tube from another end of the outer tube away from the puncture needle head to form a central tube vacant portion and central tube insertion portion of the outer tube. The central tube vacant portion is capable of bending, and during the forward or backward movement of the central tube in the outer tube along an axis of the outer tube, a bendable angle of the central tube vacant portion changes as a length of the central tube vacant portion changes.

Preferably, an expanded planar shapes of the protrusion and the notch are arc surfaces with the same arc lengths that are larger than that of a semicircle.

Preferably, end surfaces of the protrusions and the notches are curved surfaces or inclined surfaces, and the protrusions and the notches are matched via the curved surfaces or the inclined surfaces at end parts to form adjacent the segments.

Preferably, a gap for motion is provided at engagement position of a bottom of the protrusion and a top of the notch.

Preferably, a connecting line of central points of a pair of protrusions and a connecting line of central points of a pair of notches are perpendicular to each other. And an intersection line of extension surfaces of two symmetrical side surfaces of each protrusion of the pair of protrusions is central axis of the segment.

Preferably, the needle tip is an inclined surface needle tip.

Preferably, the flexible puncture needle device further comprises a transmission mechanism. The transmission mechanism is internally provided with a transmission module. The transmission module includes a transmission motor, a coupling, a threaded rod, a nut, a nut sleeve, and a guide rod. An output shaft of the transmission motor is fixedly connected with the threaded rod via a coupling. The nut is mounted on the threaded rod. The nut sleeve is fixedly sleeved on the nut. The nut sleeve is provided with a guide hole, and the nut sleeve is movably sleeved on the guide rod through the guide hole. The central tube is fixedly connected with the nut sleeve.

Preferably, the transmission mechanism further comprises a support frame. The support frame includes a front support plate, a guide rod fixing plate, a middle support plate, a rear support plate and four support rods. The middle support plate is provided with at least four through holes. Middles of the four support rods respectively pass through and are fixed in through holes of the middle support plate. Two ends of the four support rods are vertically fixed on the front support plate and the rear support plate, respectively. Guide rod fixing plate is disposed between the front support plate and the middle support plate. A guide hole is disposed on the guide rod fixing plate. A middle of guide rod passes through the guide hole in the guide rod fixing plate, and two ends of the guide rod vertically fixed to the front support plate and the middle support plate. The central tube sequentially passes through the front support plate and the guide rod fixing plate from front to back and is fixedly connected with the nut sleeve.

Preferably, the transmission mechanism further comprises a connector for connecting the puncture needle and the transmission mechanism. The connector includes a base, a base fixing plate, an elastic sleeve, a compression cap and a bracket. The base is fixed at a port of the outer tube away from the puncture needle head. Front end of the bracket is small, and rear end of the bracket is large. Rear end of the bracket is fixedly connected with a front support plate. The base fixing plate abuts against outer end of the base and is fixed inside the front end of the bracket. Front end of the compression cap is small and rear end of the compression cap is large. The compression cap is sleeved on outer side of the outer tube, and side wall of rear portion of the compression cap surrounds the base, and front end of the compression cap abuts against outer end of the base, and rear end of the compression cap is fixed to front end of the support. An elastic sleeve is disposed between the compression cap and the base.

Preferably, a central tube guide sleeve is sleeved on outer side of the central tube between the base and the nut sleeve, and two ends of the central tube guide sleeve are respectively fixed on the base fixing plate and the guide rod fixing plate.

The embodiments of present disclosure include the following advantages:

the present disclosure discloses a flexible puncture needle device including a double-layer structure of an outer tube and a central tube. The outer tube includes multiple rigid segments connected by a simple vertically engaged joints. The outer tube can freely bend towards any angles of 360 degrees, and can transmit the axial force and torque. The inner layer is a super-elastic central tube and has wide elastic deformation range. The flexible puncture needle according to the present disclosure is passively bent by the lateral force during puncture. Changing the position of central tube in the outer tube can adjust the bending rigidity of the puncture needle. When the length of the central tube in the outer tube is large, the rigidity of the puncture needle is large and the bendable angle is small. When the length of the central tube in the outer tube is small, the rigidity of the puncture needle is small and the bendable angle is large. The bendable angle of the central tube vacant portion changes as a length of the central tube vacant portion changes so as to adjust the angle of the needle head and bending direction to make the needle body bend towards a certain direction. The puncture needle device according to the present disclosure can be applied to percutaneous puncture interventional surgery, and adjust the bending angle and the bending direction during the puncture process. The puncture needle device can be integrated into a surgical robot system, and provides a flexible and accurate solution for the percutaneous puncture surgery in combination with medical imaging feedback.

DETAILED DESCRIPTION

Embodiment 1

The present embodiment 1 provides a flexible puncture needle device, the structure of which is described in detail below.

Figure 1:
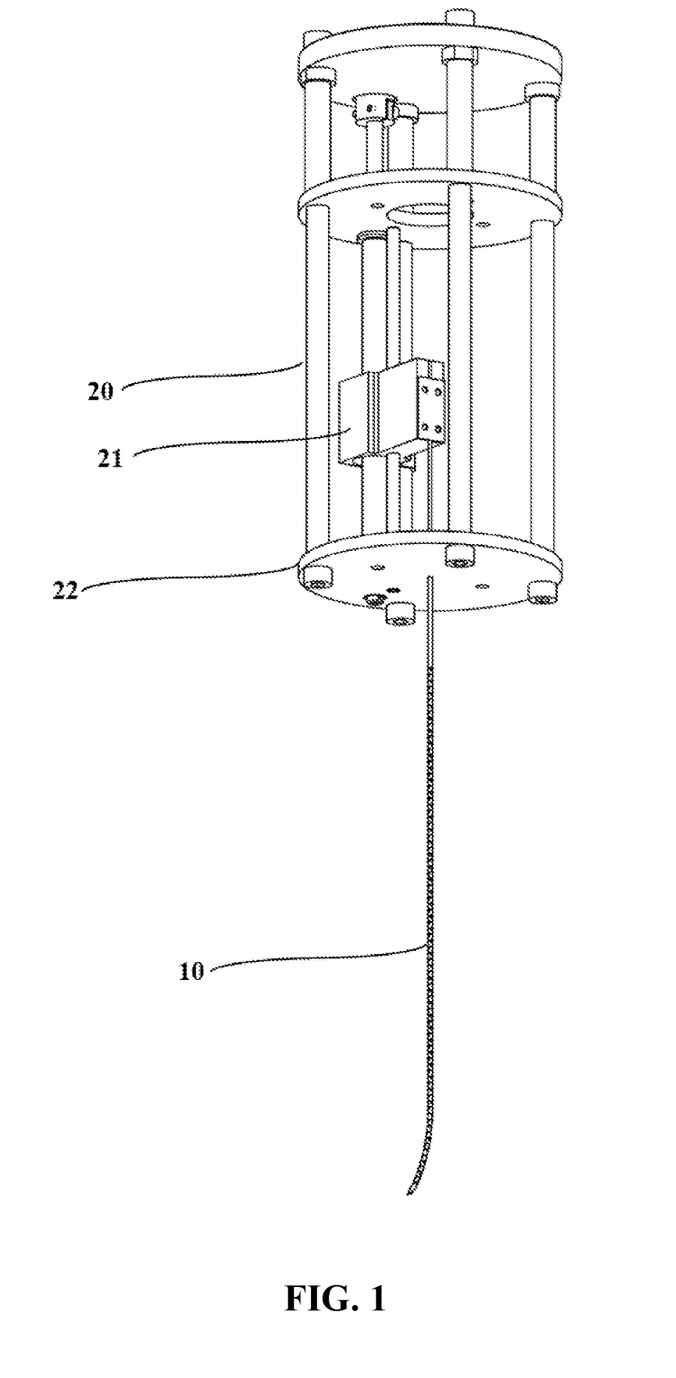
FIG. 1 is a schematic diagram of an overall structure of a flexible puncture needle device according to the present disclosure.

Referring to FIG. 1, the flexible puncture needle device includes a puncture needle 10 and a transmission mechanism 20. Transmission mechanism 20 includes a transmission module 21 and a support frame 22.

Figure 2A:
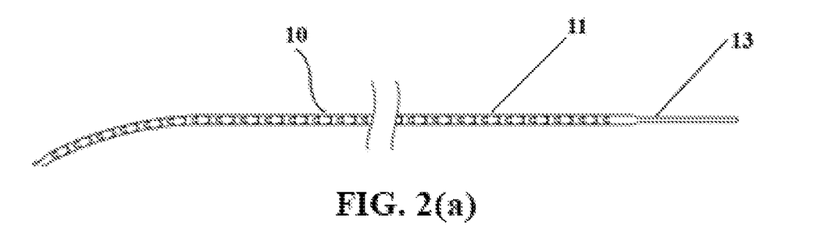
FIG. 2(a) is a schematic structural diagram of a central tube inserted into an outer tube according to the present disclosure.
Figure 2B:
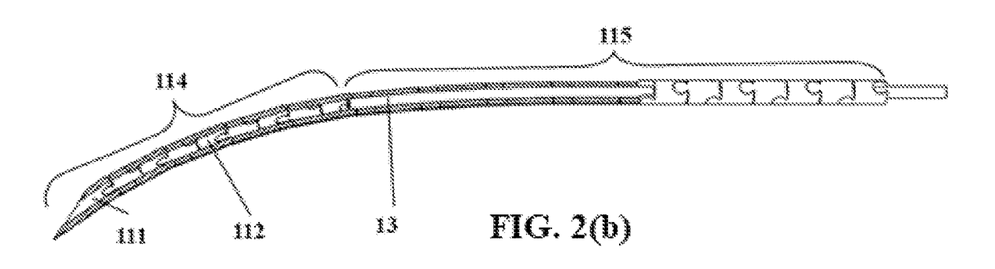
FIG. 2(b) is an enlarged structural diagram of the central tube partially inserted into the outer tube according to the present disclosure.
Figure 2C:
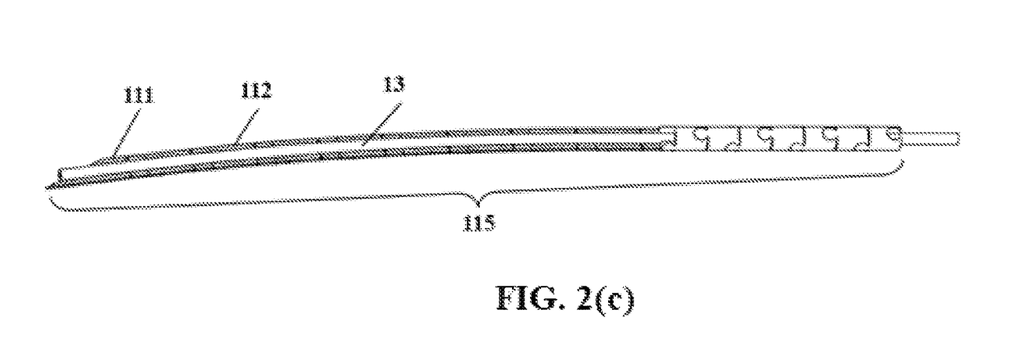
FIG. 2(c) is an enlarged structural diagram of the central tube fully inserted into the outer tube according to the present disclosure.

Referring to FIG. 2, the puncture needle 10 includes an outer tube 11 and a central tube 13. Outer tube 11 includes a puncture needle head 111 and a plurality of segments 112.

Referring to FIG. 3, a pair of protrusions 1121 and a pair of notches 1122 are provided at two ends of the segment 112, respectively. A needle tip and a pair of notches 1122 are provided at two ends of the needle head 111, respectively. A pair of protrusions 1121 of the segment 112 are engaged with a pair of notches 1122 of the puncture needle head 111 to form a needle head joint. Two adjacent segments 112 are engaged with each other via protrusions 1121 and notches 1122 to form a joint. The needle head joint and a plurality of joints are sequentially engaged to form outer tube 11 that has needle head 111 at an end and a tube body capable of bending. Central tube 13 is inserted into the outer tube 11 from another end of the outer tube 11 away from the puncture needle head 111 to form a central tube vacant portion 114 and central tube insertion portion 115 of the outer tube 11. The central tube vacant portion 114 has strong bending capacity. During the forward or backward movement of the central tube 13 in the outer tube 11 along the axis of the outer tube 11, a bendable angle of the central tube vacant portion 114 increases as a length of the central tube vacant portion 114 increases. When the puncture needle 10 is inserted into human tissue, the puncture needle head 111 cuts the tissue, under a lateral force, the central tube vacant portion 114 forms larger lateral bending, and also drives the central tube insertion portion 115 to form similar bending when it goes forward. Finally, the puncture forms a curve track.

Figure 3A:
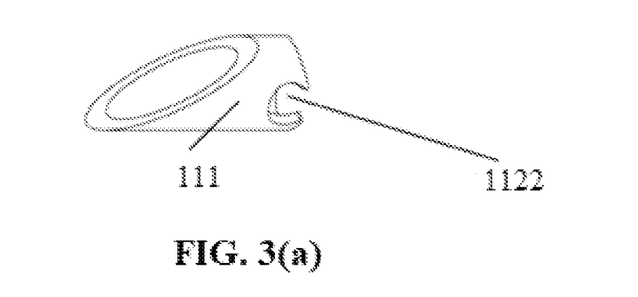
FIG. 3(a) is a schematic structural diagram of a puncture needle head according to the present disclosure.
Figure 3B:
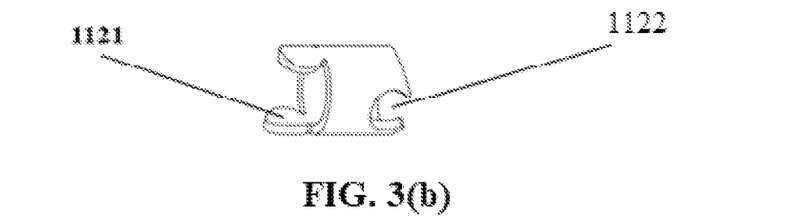
FIG. 3(b) is a schematic structural diagram of a segment according to the present disclosure.
Figure 3C:
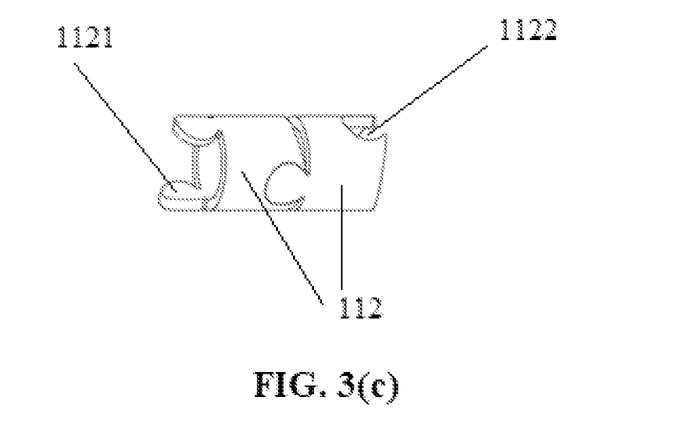
FIG. 3(c) is a schematic structural diagram of a joint in a straight state according to the present disclosure.
Figure 3D:
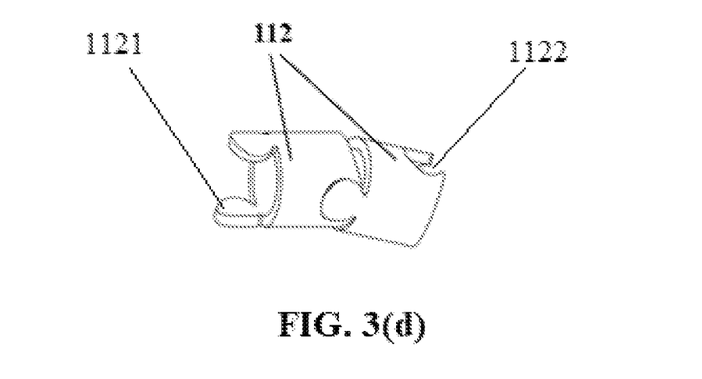
FIG. 3(d) is a schematic structural diagram of a joint in a bent state according to the present disclosure.

In order to flexibly bend the outer tube in any direction, a connecting line of central points of a pair of protrusions 1121 and a connecting line of central points of a pair of notches 1122 are perpendicular to each other. An intersection line of extension surfaces of two symmetrical side surfaces of each protrusion 1121 is central axis of the segment 112.

Figure 4A:
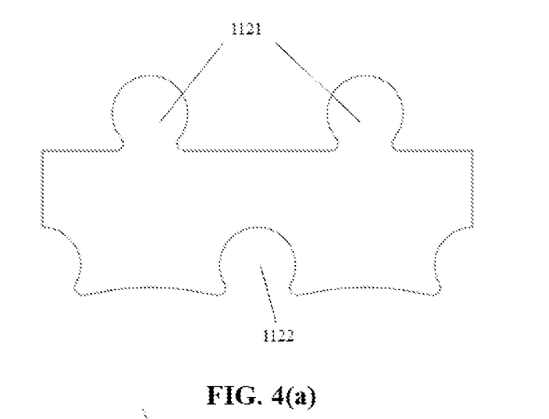
FIG. 4(a) is a schematic plan diagram of a segment according to the present disclosure.
Figure 4B:
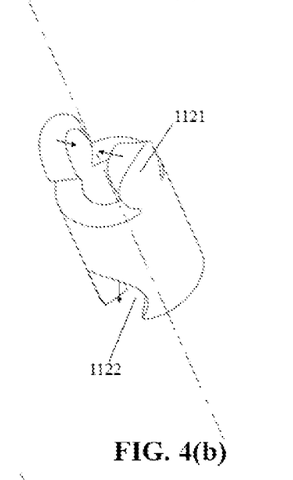
FIG. 4(b) is a schematic diagram of orientations of curved surfaces of the protrusions or notches provided by the present disclosure.
Figure 4C:
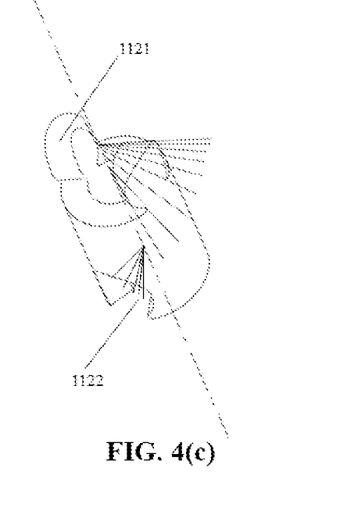
FIG. 4(c) is a schematic diagram of tangent lines of curved surfaces of a protrusion and a notch intersecting central axis of the outer tube according to the present disclosure.

In order to enhance engagement between the protrusions and the notches and achieve the effect that the engaged protrusion 1121 and the notch 1122 are not disjointed and the joint does not lose free bending, referring to FIG. 4, expanded planar shapes of the protrusion 1121 and the notch 1122 are designed to be arc surfaces with the same arc lengths that are larger than that of a semicircle. End surfaces of the protrusion 1121 and the notch 1122 in the thickness direction are curved surfaces or inclined surfaces. The outer end curved surface or inclined surface of the protrusion 1121 is inclined inwards. The inner end curved surface or inclined surface of the notch 1122 is inclined outwards. When the outer end surface of the protrusion 1121 and the inner end surface of the notch 1122 are curved surfaces, tangent lines of the end curved surfaces of the protrusion 1121 and the notch 1122 perpendicularly intersect with the central axis of the outer tube 11. The joint formed by engaging the protrusion 1121 and the notch 1122 with the end curved surfaces forms wall between the adjacent segments of outer tubes 11. When both the outer end face of the projection 1121 and the inner end face of the notch 1122 are inclined surfaces, the inclined surface of the protrusion 1121 that is inclined inward and the inclined surface of the notch 1122 that is inclined outward engage with each other to form a joint. The protrusion 1121 contacts with the notch 1122 at side surfaces, so that the segment 112 can transmit force along its central axis and torque around the central axis without disconnection. The segment 112 formed by matching the protrusion 1121 and the notch 1122 can smoothly bend, and the outer tube 11 can bend towards any direction.

Furthermore, there is a gap between the bottom of the protrusion 1121 and the top of the notch 1122. Thus, there is a gap for motion at matching position of the bottom of the protrusion 1121 and the top of the notch 1122, so that the joint formed by the protrusion 1121 and the notch 1122 can freely bend within a certain range. When a certain limit bending angle is reached, the gap is closed to prevent the segment from bending.

In order to facilitate insertion of the needle tip and provide lateral force for bending, the needle tip is an inclined surface needle tip, that is, the needle tip is provided with an inclined surface.

Preferably, the central tube 13 includes a nickel-titanium super-elastic alloy material with a Young's modulus of about 60 GPa to achieve a wide range of elastic deformation.

Figure 5A:
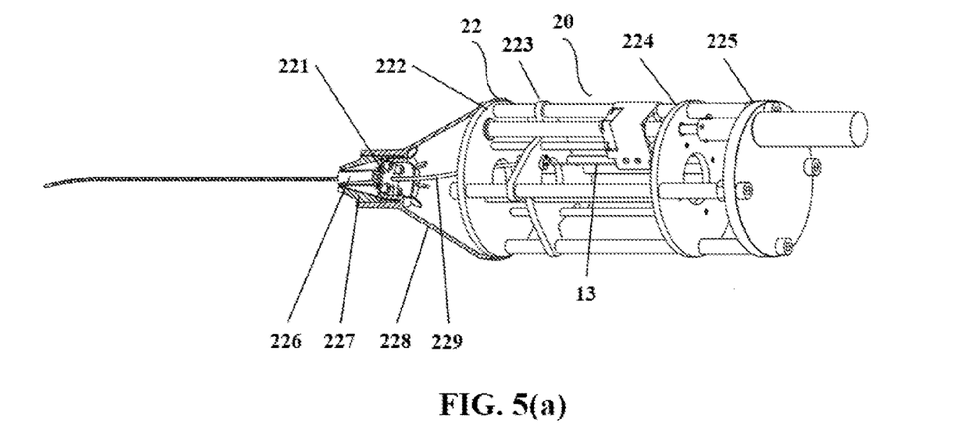
FIG. 5(a) is a schematic structural side view of a flexible puncture needle according to the present disclosure.
Figure 5B:
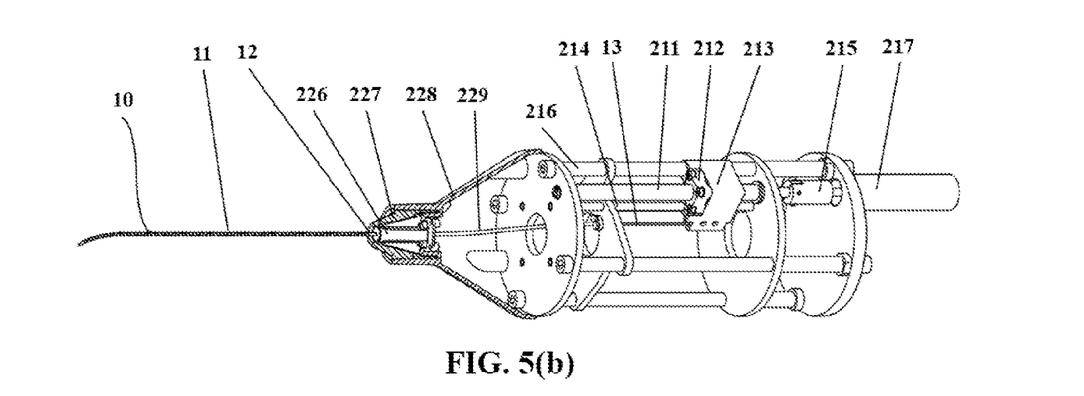
FIG. 5(b) is another schematic structural side view of a flexible puncture needle according to the present disclosure.

Referring to FIG. 5, the transmission module 21 includes a transmission motor, a coupling 215, a threaded rod 211, a nut 212, a nut sleeve 213, and a guide rod 214. The output shaft of the transmission motor is fixedly connected with the threaded rod 211 via a coupling 215. The nut 212 is mounted on the threaded rod 211. The nut sleeve 213 is fixedly sleeved on the nut 212. The nut sleeve 213 is provided with a guide hole, and the nut sleeve 213 is movably sleeved on the guide rod 214 through the guide hole. The central tube 13 is fixedly connected with the nut sleeve 213.

Specifically, the transmission motor is mounted at outer side of a rear support plate 225, and the coupling 215 is disposed at inner side of the rear support plate 225 and between the rear support plate 225 and the middle support plate 224.

Further, the support frame 22 includes a front support plate 222, a guide rod fixing plate 223, a middle support plate 224, a rear support plate 225 and four support rods 216. The middle support plate 224 is provided with at least four through holes. The middles of the four support rods 216 respectively pass through and are fixed in through holes of the middle support plate 224. Two ends of the four support rods 216 are vertically fixed on the front support plate 222 and the rear support plate 225, respectively.

Guide rod fixing plate 223 is disposed between the front support plate 222 and the middle support plate 224. A guide hole is disposed on the guide rod fixing plate 223. The middle of guide rod 214 passes through the guide hole in the guide rod fixing plate 223, and two ends of the guide rod 214 vertically fixed to the front support plate 222 and the middle support plate 224.

The central tube 13 sequentially passes through the front support plate 222 and the guide rod fixing plate 223 from front to back and is fixedly connected with the nut sleeve 213.

Figure 6:
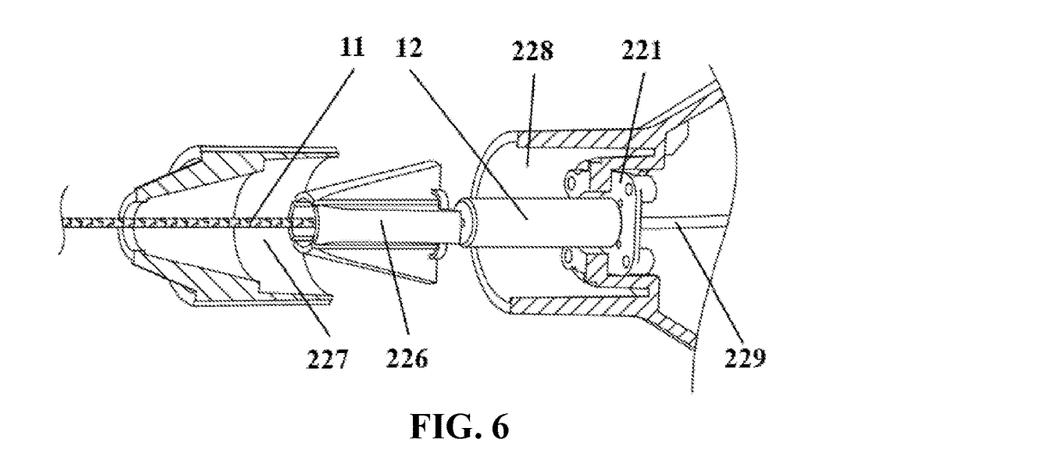
FIG. 6 is a schematic structural diagram of a connector according to the present disclosure.

Referring to FIG. 6, the transmission mechanism 20 further includes a connector for connecting the puncture needle 10 and the transmission mechanism 20. The connector includes a base 12, a base fixing plate 221, an elastic sleeve 226, a compression cap 227 and a bracket 228. The base 12 is fixed at the port of the outer tube 11 away from the puncture needle head 111. Front end of the bracket 228 is small, rear end of the bracket 228 is large. Rear end of the bracket 228 is fixedly connected with a front support plate 222. Base fixing plate 221 abuts against outer end of the base 12 and is fixed inside the front end of the bracket 228. Front end of the compression cap 227 is small and rear end of the compression cap 227 is large. The compression cap 227 is sleeved on the outer side of the outer tube 11. Side wall of rear portion of the compression cap 227 surrounds the base 12. Front end of the compression cap 227 abuts against outer end of the base 12, and rear end of the compression cap 227 is fixed to front end of the support 228. Elastic sleeve 226 is disposed between the compression cap 227 and the base 12.

Further, a central tube guide sleeve 229 is sleeved on outer side of a central tube 13 between the base 12 and the nut sleeve 213. Two ends of the central tube guide sleeve 229 are respectively fixed on the base fixing plate 221 and the guide rod fixing plate 223.

The present disclosure discloses a flexible puncture needle device including a double-layer structure of an outer tube and a central tube. The outer tube includes multiple rigid segments connected by a simple vertically engaged joints. The outer tube can freely bend towards any angles, and can transmit the axial force and torque. The inner layer is a super-elastic central tube and has wide elastic deformation range. The flexible puncture needle is passively bent by the lateral force during puncture. Changing the position of central tube in the outer tube can adjust the bending rigidity of the puncture needle. When the length of the central tube in the outer tube is large, the rigidity of the puncture needle is large and the bendable angle is small. When the length of the central tube in the outer tube is small, the rigidity of the puncture needle is small and the bendable angle is large. The axial rotation of the puncture needle can change the direction of lateral force on the needle head, so that the passive bending of the needle body is realized. Therefore, the needle body can be bent, and the angle of the needle head can be adjusted.

In addition, the present disclosure provides a transmission mechanism. The transmission mechanism is fixedly connected with the flexible puncture needle. The flexible puncture needle can rotate along with the transmission mechanism and is fed. The transmission mechanism can drive the central tube in the flexible puncture needle to move forwards or backwards in the flexible puncture needle, so that the rigidity of the flexible puncture needle is changed with the change of the length of the central tube in the outer tube.

The disclosure is only described with reference to the embodiments above. The structure, the arrangement position and the connection of each component can be changed. On the basis of the technical solutions of the disclosure, improvement and equivalent transformation of individual components according to the principle of the disclosure are not excluded from the protection scope of the disclosure.

The invention claimed is:

1. A flexible puncture needle device, comprising a puncture needle (10) and a transmission mechanism (20), wherein
the puncture needle (10) comprises an outer tube (11) and a central tube (13);

the outer tube (11) comprises a puncture needle head (111) and a plurality of segments (112) sequentially engaged with each other and connected, at front end of the outer tube (11), with the puncture needle head (111);

the central tube (13) is inserted into the outer tube (11) from rear end of the outer tube (11) to form a central tube vacant portion (114) and central tube insertion portion (115) of the outer tube (11);

the central tube vacant portion (114) is capable of bending, and during the forward or backward movement of the central tube (13) in the outer tube (11) along an axis of the outer tube (11), a bendable angle of the central tube vacant portion (114) changes as a length of the central tube vacant portion (114) changes;

the transmission mechanism (20) comprises a connector for connecting the puncture needle (10) and the transmission mechanism (20); and the connector includes a base (12) fixed at a rear port of the outer tube (11).

2. The flexible puncture needle device of claim 1, wherein the puncture needle head (111) includes a needle tip at front end and a pair of notches (1122) or a pair of protrusions (1121) at rear end, and a pair of protrusions (1121) and a pair of notches (1122) are formed at two ends of each segment from the plurality of the segments (112), respectively;

a pair of protrusions (1121) or a pair of notches (1122) at an end of one segment (112) from the plurality of segments are engaged with a pair of notches (1122) or a pair of protrusions (1121) at rear end of the puncture needle head (111) to form a needle head joint, two adjacent segments (112) from the plurality of segments are engaged with one another via the notch (1122) or protrusion (1121) from each adjacent segments being engaged to form a joint, and the needle head joint and a series of adjacent segments forming a plurality of joints sequentially engaged with each other from head to tail to form an outer tube (11) with the puncture needle head (111) at front end and a tube body capable of axially bending.

3. The flexible puncture needle device of claim 2, wherein end surfaces of the protrusions (1121) and the notches (1122) from a segment from the plurality of segments are curved surfaces or inclined surfaces, and the protrusions (1121) and the notches (1122) from adjacent segments from the plurality of segments are matched via the curved surfaces or the inclined surfaces at end parts.

4. The flexible puncture needle device of claim 2, wherein a gap for motion is provided at engagement position of a bottom of the protrusion (1121) from one segment from the plurality of segments and a top of the notch (1122) from an adjacent segment from the plurality of segments.

5. The flexible puncture needle device of claim 2, wherein a connecting line of central points of a pair of protrusions (1121) from a segment from the plurality of segments and a connecting line of central points of a pair of notches (1122) from the segment from the plurality of segments are perpendicular to each other; or an intersection line of extension surfaces of two symmetrical side surfaces of each protrusion (1121) from a segment from the plurality of segments of the pair of protrusions (1121) is central axis of the segment (112).

6. The flexible puncture needle device of claim 2, wherein the needle tip is an inclined surface needle tip.

7. The flexible puncture needle device of claim 1, wherein the transmission mechanism (20) further comprises a transmission module (21), the transmission module (21) includes a threaded rod (211), a nut (212), and a nut sleeve (213), the nut (212) is mounted on the threaded rod (211);

the nut sleeve (213) is fixedly sleeved on the nut (212); and the central tube (13) is fixedly connected with the nut sleeve (213).

8. The flexible puncture needle device of claim 7, wherein the transmission mechanism (20) further comprises a support frame (22), the support frame (22) includes a front support plate (222), a rear support plate (225) and a plurality of support rods (216), two ends of each of the plurality of support rods (216) are vertically fixed on the front support plate (222) and the rear support plate (225), respectively.

9. The flexible puncture needle device of claim 7, comprising a central tube guide sleeve (229) sleeved on outer side of the central tube (13) between the base (12) and the nut sleeve (213), and two ends of the central tube guide sleeve (229) are respectively fixed on a base fixing plate (221) and a guide rod fixing plate (223).

10. The flexible puncture needle device of claim 2, wherein an expanded planar shapes of the protrusion (1121) from a segment from the plurality of segments and the notch (1122) from the segment from the plurality of segments are arc surfaces with the same arc lengths that are larger than that of a semicircle.

11. The flexible puncture needle device of claim 7, wherein the transmission module (21) further includes a guide rod (214), the nut sleeve (213) is provided with a guide hole, and the nut sleeve (213) is movably sleeved on the guide rod (214) through the guide hole.

12. The flexible puncture needle device of claim 7, wherein the transmission module (21) further includes a transmission motor and a coupling (215), and an output shaft of the transmission motor is fixedly connected with the threaded rod (211) via the coupling (215).

13. The flexible puncture needle device of claim 8, wherein the support frame (22) further includes a guide rod fixing plate (223) and a middle support plate (224), the middle support plate (224) is provided with a plurality of through holes, the plurality of the support rods (216) respectively pass through and are fixed in the plurality of through holes of the middle support plate (224);

the guide rod fixing plate (223) is disposed between the front support plate (222) and the middle support plate (224), a guide hole is disposed on the guide rod fixing plate (223), a guide rod (214) passes through the guide hole in the guide rod fixing plate (223), and two ends of the guide rod (214) vertically fixed to the front support plate (222) and the middle support plate (224); and the central tube (13) sequentially passes through the front support plate (222) and the guide rod fixing plate (223) from front to back and is fixedly connected with the nut sleeve (213).

14. The flexible puncture needle device of claim 1, wherein the connector further includes a compression cap (227) and a bracket (228), front end of the bracket (228) is smaller than rear end of the bracket (228), the rear end of the bracket (228) is fixedly connected with a front support plate (222);

front end of the compression cap (227) is smaller than rear end of the compression cap (227), the compression cap (227) is sleeved on outer side of the outer tube (11), and side wall of rear portion of the compression cap (227) surrounds the base (12), and front end of the compression cap (227) abuts against outer end of the base (12), and rear end of the compression cap (227) is fixed to front end of the bracket (228).

15. The flexible puncture needle device of claim 14, wherein the connector further includes a base fixing plate (221) abutting against outer end of the base (12) and fixed inside the front end of the bracket (228).

16. The flexible puncture needle device of claim 14, wherein the connector further includes an elastic sleeve (226) disposed between the compression cap (227) and the base (12).

* * * * *